United States Patent
Adams et al.

(10) Patent No.: US 10,076,480 B2
(45) Date of Patent: Sep. 18, 2018

(54) WET SKIN MOISTURIZER PRODUCT

(71) Applicant: Kao USA Inc., Cincinnati, OH (US)

(72) Inventors: Lisa Adams, Mason, OH (US);
Kimberly Bauman, Union Township, OH (US); Andrew Dimuzio, Symmes Township, OH (US); Akira Fuji, Florence, KY (US)

(73) Assignee: Kao USA, Inc, Cincinnati, OH (US)

( * ) Notice: Subject to any disclaimer, the term of this patent is extended or adjusted under 35 U.S.C. 154(b) by 2 days.

(21) Appl. No.: 15/341,709

(22) Filed: Nov. 2, 2016

(65) Prior Publication Data

US 2018/0116932 A1    May 3, 2018

(51) Int. Cl.
| | |
|---|---|
| *A61K 8/41* | (2006.01) |
| *A61K 8/42* | (2006.01) |
| *A61K 8/891* | (2006.01) |
| *A61K 8/90* | (2006.01) |
| *A61Q 19/00* | (2006.01) |

(52) U.S. Cl.
CPC ............... *A61K 8/416* (2013.01); *A61K 8/42* (2013.01); *A61K 8/891* (2013.01); *A61K 8/90* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 5,221,534 | A | 6/1993 | DesLauriers et al. |
| 5,578,299 | A | 11/1996 | Starch |
| 5,888,492 | A | 3/1999 | Starch |
| 9,301,914 | B1 | 4/2016 | Rustici et al. |

FOREIGN PATENT DOCUMENTS

EP      2 181 694 A1     5/2010

OTHER PUBLICATIONS

Paez, A., et al., "Cationic emulsifiers: an emerging trend in skin care," Cosmetics and Toiletries Manufacture Worldwide, 2004, pp. 67-71.

*Primary Examiner* — Matthew P Coughlin
*Assistant Examiner* — Thurman M Wheeler
(74) *Attorney, Agent, or Firm* — Frost Brown Todd, LLC

(57) ABSTRACT

A wet skin moisturizer (WSM) composition, in the form of an oil-in-water emulsion, contains the following components: a cationic emulsifier (such as behentrimonium chloride), a skin conditioner component (such as behenamidopropyl dimethylamine), and a block copolymer which comprises at least one segment derived from a thermoplastic monomer chosen from thermoplastic monomers, thermoplastic comonomers and mixtures thereof (such as a mixture of ethylene/propylene/styrene copolymer and butylene/ethylene/styrene copolymer). This composition is applied to previously-wetted skin following a shower or bath, after which the moisturized skin is dried. The composition blends nicely with the water on the skin to provide an even film that does not feel greasy on the skin and which provides the skin with hydration and skin conditioning benefits.

16 Claims, No Drawings

WET SKIN MOISTURIZER PRODUCT

BACKGROUND

Hydration is a key factor in maintaining the skin barrier and relieving dry skin. It can be delivered most effectively through the use of a topical moisturizer containing humectants (such as glycerin), occlusive agents (such as petrolatum), and barrier-supporting materials (such as ceramides or pseudo-ceramides). Additionally, pH can be an important factor in delivering hydration to the skin. Moisturizers are typically a blend of many ingredients and generally need to include an emulsifier to create a homogeneous mixture. An ingredient sometimes used for emulsification in moisturizers is behentrimonium chloride.

The purpose of a wet skin moisturizer (WSM) is to deliver key ingredients needed for relieving dry skin. It is generally recommended to apply moisturizers within three minutes after showering or bathing to help trap in moisture delivered to the skin from the shower or bath. The WSM is designed to be used prior to toweling off on just-cleansed and wet skin. The ingredients blend nicely with the water on the skin to provide an even film that does not feel greasy on the skin. Since the stratum corneum has been hydrated and swollen from the shower, water content is increased and the WSM seals in the moisture, allowing for long-lasting and deeper hydration within the stratum corneum. The WSM of the present invention is an oil-in-water emulsion that can contain some or all of the following or similar components: behentrimonium chloride for emulsification and adhesion of the emulsion to the skin; glycerin for skin hydration; skin conditioners (such as behenamidopropyl dimethylamine); branched-chain fatty esters; block copolymers; mineral oil; rheology modifiers, such as polyquaternium-37; a pH adjuster, such as lactic acid; and a linear siloxane.

Existing moisturizers that are utilized in the shower are designed to wash off the skin. They deposit occlusive materials and trap water vapor without delivering hydration into deeper layers of the stratum corneum. These products include Nivea-In-Shower and Eucerin-In-Shower. Additionally, Jergens Wet Skin Moisturizer is designed with similar components to the WSM herein, but may not provide as much substantivity of lipids to the skin since it does not include the cationic surfactant, behentrimonium chloride, or the lower pH of the WSM.

In the WSM of the present invention, the emulsion spreads extremely well when applied to wetted skin, and provides enhanced and long-lasting moisturizing effects. Moreover, the inventors have found that the oil-in-water emulsion of the present invention preferably is not rinsed off after application to wetted skin, and after drying, the composition can provide excellent, long-lasting skin benefits.

The body cosmetics of the present invention spread extremely well when applied directly to wetted skin, and provide good moisturizing effects after application, such as a moist feeling and a smooth feeling, which last for a long time after application. In addition, the body cosmetics can show the above-described excellent effects simply by being applied to wetted skin and then towel drying. Hence, they can provide these effects by simple processes after bathing. In addition, the product does not leave a greasy residue on the skin; such a greasy residue does not provide a good feeling after the skin has been cleansed.

SUMMARY

The present invention therefore relates to a skin conditioning composition which comprises:

(A) at least one block copolymer which comprises one or more segments derived from at least one monomer chosen from thermoplastic monomers, thermoplastic comonomers, and mixtures thereof;
(B) at least one cationic emulsifier (such as behentrimonium chloride); and
(C) at least one amidoamine (such as a fatty acid amidopropyl dimethylamine).

The present invention also relates to a method for moisturizing skin comprising applying an effective amount of a skin conditioning composition to skin wetted with water, and then drying the skin after application of the skin conditioning composition, wherein the skin conditioning composition comprises the following components:
(A) at least one block copolymer which comprises one or more segments derived from one or more monomers chosen from thermoplastic monomers, thermoplastic comonomers, and mixtures thereof;
(B) at least one cationic emulsifier; and
(C) at least one amidoamine.

As used herein, all percentages and ratios are "by weight" unless otherwise specified. Further, all patents and other printed publications referred to in this application are incorporated by reference herein in their entirety.

DETAILED DESCRIPTION

The WSM skin conditioning compositions of the present invention are generally in the form of an oil-in-water emulsion, and generally contain at least the following components: a cationic emulsifier, a mono-long chain amidoamine, and a block copolymer. Each of these components will be discussed in greater detail below. Other components typically found in skin conditioning compositions may also be included in the compositions of the present invention, at their conventional usage levels.

The cationic emulsifier component provides emulsification in the formation of the oil-in-water emulsion, and also provides adhesion of the moisturizing components to the skin of the user. The compositions of the present invention typically include from about 0.3% to about 3%, such as from about 0.3% to about 1.5%, of the cationic emulsifier component. Cationic emulsifiers are well-known in the detergent and skin care arts. Examples of such known emulsifiers include mono-long chain quaternary ammonium materials, such as behentrimonium chloride, or di-long chain quaternary ammonium materials, such as distearyldimonium chloride. The long-chains utilized in the quaternary ammonium materials typically contain from about 14 to about 24 carbon atoms. When formulating quaternary ammonium materials useful herein, any of the skin compatible anions, such as chloride, bromide, or methylsulfate, can be paired with the cationic portion of the molecule. Another type of cationic emulsifier useful herein is a mono-long chain amidoquat material. This is a material where one chain on the ammonium group is a fatty acid which includes an amido group. An example of such a material is palmitamidopropyltrimonium chloride. Examples of materials useful as the cationic emulsifier in the present invention include behentrimonium chloride (commercially available, for example, as Varisoft BT-85), distearyldimonium chloride (commercially available as Varisoft TA-100), and palmitamidopropyltrimonium chlorine (commercially available as Varisoft PATC). Mixtures of these materials can also be used.

The second component in the compositions of the present invention is a mono-long chain ($C_{14}$-$C_{24}$) amidoamine. This component acts as a skin conditioner and provides a skin softening benefit to the user. It would typically be included in the composition of the present invention at from about 0.3% to about 3.0%. Such amidoamines are well-known and are used extensively in the cosmetics and hair care industries. They are typically formed from fatty acids and diamines. These compounds generally include a fatty acid chain which incorporates an amido linkage; that long-chain group is hooked to an amine moiety having two shorter chains (e.g., methyl or ethyl) attached. An example of such a material is a fatty acid amidopropyl dimethylamine, such as, for example, behenamidopropyl dimethylamine, isostearamidopropyl dimethylamine, linoleamidopropyl dimethylamine, myristamidopropyl dimethylamine, oleamidopropyl dimethylamine, ricinoleamidopropyl dimethylamine, and stearamidopropyl dimethylamine, and mixtures of such materials.

In exemplary compositions of the present invention the weight ratio of the cationic emulsifier component to the amidoamine component is from about 4:1 to about 1:6, preferably from about 2:1 to about 1:2.

The third component of the compositions of the present invention is a block copolymer which comprises at least one segment derived from one or more monomers chosen from thermoplastic monomers, thermoplastic comonomers, and mixtures thereof. As used herein, "thermoplastic" means a material (especially a synthetic resin) which becomes plastic upon heating and hardens on cooling, and is able to repeat these properties on successive heatings and coolings. This component is typically included in the compositions of the present invention at from about 1% to about 10%, such as from about 2% to about 7%, by weight of the composition. The component is a film-former and it contributes to a unique feel (glide) when applied to the skin.

The di- or tri-block copolymers utilized in the present invention are described in U.S. Pat. No. 5,888,492, Starch, issued Mar. 30, 1999, and U.S. Pat. No. 5,221,534, Des Lauriers, et al, issued Jun. 22, 1993, both of which are incorporated herein by reference. The di- and tri-block copolymers are comprised of styrenic monomers and low glass transition temperature (Tg) monomers, such as butadiene and isoprene. Suitable di-block and tri-block polymers are those commercially available from Shell Chemical Company as the Kraton D and Kraton G product lines. Particularly preferred are Kraton G 1650, a styrene/ethylene-butylene/styrene tri-block copolymer, and Kraton G 1702, an ethylene/propylene/styrene di-block copolymer.

The term "styrenic" in the context of the present application denotes styrene as well as substituted styrene, such as ortho-, meta-1 and pure-alkyl-styrene, and x-alkyl-styrene, where alkyl denotes a $C_1$-$C_3$ alkyl group.

This copolymer may be admixed with a lipid-based material such as mineral oil to form a gel material which is not only easy to incorporate into the compositions of the present invention but also provides a sharply improved skin conditioning effect, when compared to the use of hydrocarbon oil formulations in non-rinse-off environments. The use of the polymer together with the hydrocarbon oil not only improves viscosity properties, such that the product can be applied in the shower, without rinsing off, but, after rinsing, skin conditioning effects are improved.

A mineral oil gel, of the type described in U.S. Pat. No. 5,221,534, may also be used. A suitable, commercially available gel for this type of approach are the Geahlene gels available from Penreco, a division of Penzoil Products Company. An exemplary commercially-available gel is Geahlene 500, which is a mixture of mineral oil, polystyrene-poly(ethylene/butylene)—polystyrene tri-block copolymer and poly-(ethylene/propylene)—polystyrene di-block copolymer. An example of a material which may be used in the present invention is a mixture of mineral oil, ethylene/propylene/styrene copolymer together with butylene/ethylene styrene copolymer.

Generally, the compositions of the present invention have a pH of from about 3 to about 6, for example, from about 4 to about 5 (measured at about 25° C.). The pH can be adjusted within this range by the addition of an acid material, such as lactic acid, which is compatible with the skin and the other components of the composition.

The compositions of the present invention include a carrier, such as water and/or ethanol, generally at a level of from about 25% to about 90%, preferably from about 35% to about 75% of the composition.

The compositions of the present invention may also include additional emollient and humectant components, such as one or more fatty acid esters, fatty alcohols (such as glycerin) or fatty acids, or silicones. Since the emollient properties contributed by these materials are not required for the skin conditioning effects of the invention, this element is optional and can be included, on a weight basis, at from 0 to about 40% of the composition as a whole. The emollient or humectant can also be used to modify the "feel" or "aesthetics" of the deposit on the skin. The emollient(s) should be liquid at room temperature, or form a liquid preparation when added to the remainder of the composition. Composition blending is facilitated by selecting an emollient(s) which is liquid at room temperature.

There are a wide variety of fatty acid esters which meet the described requirements. Suitable esters will be selected, in appropriate weight amounts, to stay within aesthetically acceptable limits. Throughout this application, references are made to "fatty" carbon-based compounds and compositions, such as fatty acids and fatty alcohols. This term is intended to refer to substantially water-insoluble compounds.

Suitable fatty esters include fatty acids of monohydric alcohols have the general formula $R_1$—O—C—O—$R_2$, wherein $R_1$ and $R_2$ are hydrocarbon chains derived from animal and/or vegetable fats and oils or petroleums. Suitable examples include isopropyl palmitate, isopropylmyristate, iso-propylstearate, octyl isononanoate, isocetyl stearate, oleyl oleate, isohexyl neopentanoate, myristyl neopentanoate, myristyl propionate, decyl oleate, cetearyl octanoate, octyl palmitate, isodecyl oleate, octyl hydroxystearate, cetyl octanoate, isostearyl octanoate, and mixtures thereof, wherein octyl and octanoate moieties may be straight chain or branched, such as 2-ethylhexyl.

Fatty esters of ethoxylated monohydric alcohols having the general formula $R_1$—O—$(CH_2CH_2O)_x$—CO—$R_2$, wherein $R_1$ and $R_2$ are defined as above, and x is 1-30, may also be employed. Suitable examples include myreth-3 laurate, laureth-2 octanoate (straight or branched), myreth-3 myristate, and myreth-3 palmitate.

Instead of simple esters, di- and tri-esters of monohydric alcohols of the type described above, that is, esters of fatty alcohols and polycarboxylic acids, may be employed. Examples include diisopropyl adipate, diisostearyl fumarate, triisostearyl trilinoleate, diisopropyl sebacate, diisostearyl dilinoleate, trioctylcitrate (straight or branched), diisopropyl dilinoleate, and triisostearyl citrate.

In the alternative, rather than using polycarboxylic acids, polyhydric alcohols may be employed in the preparation of fatty esters for use as the ester component of this invention. Examples include propylene glycol dipelargonate, glyceryl isostearate, neopentyl glycol dicaprate, trioctenonin glyceryl trioctenoate, triolein, propylglycol laurate, neopentyl glycol dioctanoate, and triisostearin (glyceryl triisostearate), wherein octanoate moieties may be straight or branched chain.

Of course, related esters comprised of selections from the fatty acids and alcohols identified, as well as mixtures of the fatty esters identified, may be employed in the present invention.

propenamide; and C1-30-acylpoly (oxyethylene)-2-methyl-2-propenoate quaternized with diethyl sulfate; and mixtures thereof.

The following table lists examples of components which can be used in the compositions of the present invention, together with the function provided by those components in the composition, as well as examples of the effective percentage range of use for those components.

| Material | Effective Percentage Range | Comment |
| --- | --- | --- |
| Versagel M200 | 1.00-10.00% | Film former, contributes to unique application feel ("glide") |
| Behenamidopropyl Dimethylamine | 0.30-1.00% | Skin softening benefit |
| Behentrimonium Chloride | 0.30-3.00% | Adhesion benefit |
| Shea Butter | 0.50-5.00% | Skin conditioning benefit |
| Polyquaternium-37 | 0.05-0.30% | Contributes to unique application feel ("glide") |
| Lactic Acid | 0.05-0.50% | Lower pH contributes to adhesion and skin softness |
| Glycerin | 5.00-30.00% | Provides long lasting moisture |
| Allatoin | 0.1-1.0% | Provides anti-irritant effects |
| Panthenol | 0.1-1.0% | Provides anti-irritant effects |
| Petrolatum | 0.50-10.00% | Provides occlusion, film former |
| Cetyl PG-Hydroxyethylpamitamide | 0.01-3.00% | Unique ceramide technology |
| Trisiloxane and Dimethicone | 0.10-5.00% | Provides unique after feel (non-greasy) |
| Paraffin | 0.10-5.00% | Contributes to structure |
| Isopropyl Palmitate | 1.00-10.00% | Skin Softening benefit |
| Ethylhexyl Isononanoate | 1.00-10.00% | Skin Softening benefit |
| C-12, 15 Alkyl Benzoate | 1.00-10.00% | Skin Softening benefit |

Instead of, or in addition to, the esters described above, branched chain fatty alcohols or acids liquid at room temperature may be used, if soluble in the compositions of the present invention. Representative members of this class include isostearic acid, butyloctenoic acid, hexyl decanoic acid, octododecanoic acid, decyl dodecanoic acid, butyl octanol, hexyl decanol, octododecanol and decyl dodecanol.

A different class of emollients which may be used in place of the esters, acids and alcohols described above, or together therewith, is synthetic liquid silicone polymers having a monomer of the general structure

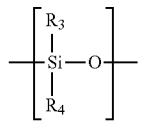

wherein $R_3$ and $R_4$ are lower alkyl groups having one to six carbon atoms. Such materials are well-known in the skin care art. Examples of suitable liquid silicone polymers include dimethicone, dimethiconol and cyclomethicone.

Examples of emollients and humectants useful in the present invention include glycerin (to provide skin hydration), branched fatty esters, fatty alcohols, petrolatum, mineral oil, or linear siloxanes, to provide skin conditioning benefits to the user. Mixtures of these materials can be used.

The compositions of the present invention may also include rheology modifiers, well-known in the skin care art, such as polyquaternium-37 or paraffin, used at its conventional level.

The compositions of the present invention may also include cationic film-forming materials to provide skin conditioning benefits to the user. Such materials are well-known in the skin care art and include, for example, ethanaminium; N,N,N-trimethyl-2-((2-methyl-1-oxo-2-propenyl) oxy) homopolymer; 2-(N,N-dimethylamino) ethyl-2-methyl-2-propenoate; polymer with N,N-dimethyl-2-

Conventional cosmetic additives may be added to the skin conditioner compositions of the present invention at their conventional usage levels. Principle among these are fragrances, antioxidants, preservatives and pigments or colorants. Additional active agents, such as antibiotics, including bacteriostats and anti-fungal agents, may also be incorporated if compatible with and complimentary to the composition. Specifically, these additional additives will be incorporated in limited weight amounts selected so as not to interfere with the viscosity, "feel" and "rinse-off" characteristics of the base composition. Such additives and their usage levels are conventional to those skilled in the skin care art.

The composition of the present invention is prepared by simple blending of the various formulation components, pursuant to art-recognized technology. Certain copolymers may require limited heating for thorough blending, as discussed in U.S. Pat. No. 5,221,534.

The present invention also encompasses the method of using the compositions of the present invention. In this method, an effective amount of the skin conditioning composition of the present invention is applied to skin which has been wetted with water (such as from a shower or bath) and then, after application of the composition, the skin may be dried (for example, towel dried). By "effective amount", as used herein, is meant an amount sufficient to provide the skin conditioning benefits of the present invention when applied to the skin. An example of such a "skin conditioning effective amount" constitutes from about 5 to about 15 grams of composition per application. The composition can be reapplied periodically when needed to provide the desired skin conditioning benefits.

EXAMPLE

A composition of the present invention is made having the following components in the amounts stated:

| Name | % W/W |
| --- | --- |
| Deionized Water | to 100 |
| Glycerin USP | 15 |
| Isopropyl Palmitate | 5 |
| Versagel M200 | 6 |
| Ethylhexyl Isononanoate | 3 |
| Cetearyl Alcohol | 3 |
| C12-15 Alkyl Benzoate | 1 |
| Cetyl-PG Hydroxyethyl Palmitamide | 0.55 |
| Behentrimonium Chloride | 0.75 |
| Behenamidopropyl Dimethylamine | 0.4 |
| Benzalkonium Chloride | 0.1 |
| Preservative | 0.5 |
| Polyquaternium-37 | 0.2 |

The composition is made as follows:

Combine the above materials, except the preservative, in a vessel large enough to hold the batch. Heat, while mixing, to 80° C. Add the preservative and continue to heat. Cool the product with chilled water for about 60 minutes.

This composition is used as follows: after stepping out of the shower, the consumer applies about 12 grams (a small palm full) of the composition to the wet skin and rubs it into the skin. Following application, the skin is towel-dried. The composition is quickly absorbed into the skin and provides a skin conditioning benefit to the user without leaving a greasy feel on the skin.

What is claimed is:

1. A skin conditioning composition comprising:
   (A) at least one block copolymer which comprises at least one segment derived from a monomer chosen from thermoplastic monomers, thermoplastic comonomers, and mixtures thereof;
   (B) at least one cationic emulsifier selected from the group consisting of mono-long chain quaternary ammonium materials, di-long chain quaternary ammonium materials and mixtures thereof; and
   (C) at least one fatty acid amidopropyl dimethylamine.

2. A composition according to claim 1 wherein the ratio (by weight) of cationic emulsifier (B) to fatty acid amidopropyl dimethylamine (C) is from about 4:1 to about 1:6.

3. A composition according to claim 2 wherein the ratio (by weight) of cationic emulsifier (B) to fatty acid amidopropyl dimethylamine (C) is from about 2:1 to about 1:2.

4. A composition according to claim 1 wherein the cationic emulsifier is selected from the group consisting of behentrimonium salt, distearyldimonium salt, palmitamidopropyltrimonium salt, and mixtures thereof.

5. A composition according to claim 4 wherein the cationic emulsifier is present from about 0.3% to about 3% (by weight) of the composition.

6. A composition according to claim 1 wherein the fatty acid amidopropyl dimethylamine is selected from the group consisting of behenamidopropyl dimethylamine, isostearamidopropyl dimethylamine, linoleamidopropyl dimethylamine, myristamidopropyl dimethylamine, oleamidopropyl dimethylamine, ricinoleamidopropyl dimethylamine, and stearamidopropyl dimethylamine, and mixtures thereof.

7. A composition according to claim 1 which additionally contains a cationic film former.

8. A composition according to claim 7 wherein the cationic film former is selected from the group consisting of Ethanaminium, N, N, N-trimethyl-2-(2-methyl-1-oxo-2-propenyl)oxy)-chloride, homopolymer, 2-(N,N-dimethylamino)ethyl 2-methyl-2-propenoate, polymer with N,N-dimethyl-2-propenamide, and C1-30-acylpoly(oxyethylene) 2-methyl-2-propenoate quaternized with diethyl sulfate, and mixtures thereof.

9. A composition according to claim 1 having a pH of from about 3 to about 6.

10. A composition according to claim 1 further comprising silicone.

11. A composition according to claim 10 wherein said silicone is present from about 0.5% to about 5%, by weight of the composition.

12. A composition according to claim 11 wherein the silicone is selected from dimethicone, dimethiconol, cyclomethicone and mixtures thereof.

13. A composition according to claim 12 wherein the silicone is dimethicone.

14. A composition according to claim 1 which comprises from about 1% to about 10% of a mixture of ethylene/propylene/styrene copolymer and butylene/ethylene/styrene copolymer; from about 0.3% to about 3% of a behentrimonium salt; and from about 0.3% to about 3% of the fatty acid amidopropyl dimethylamine.

15. A method comprising applying an effective amount of a skin conditioning composition to skin wetted with water and then drying the skin, wherein the body cosmetic comprises the following components:
   (A) at least one block copolymer which comprises at least one segment derived from a monomer chosen from thermoplastic monomers, thermoplastic comonomers, and mixtures thereof;
   (B) at least one cationic emulsifier selected from the group consisting of mono-long chain quaternary ammonium materials, di-long chain quaternary ammonium materials and mixtures thereof; and
   (C) at least one fatty acid amidopropyl dimethylamine.

16. The method according to claim 15 wherein the skin conditioning composition comprises from about 1% to about 10% of a mixture of ethylene/propylene/styrene copolymer and butylene/ethylene/styrene copolymer; from about 0.3% to about 3% of a behentrimonium salt; and from about 0.3% to about 3% of the fatty acid amidopropyl dimethylamine.

* * * * *